United States Patent [19]
Kulprathipanja et al.

[11] Patent Number: 5,962,735
[45] Date of Patent: Oct. 5, 1999

[54] METHOD FOR TREATING AN ORGANIC LIQUID CONTAMINATED WITH AN IODIDE COMPOUND

[75] Inventors: Santi Kulprathipanja, Inverness; Benjamin C. Spehlmann, Arlington Heights; Richard R. Willis, Cary; John D. Sherman, Inverness; William A. Leet, Naperville, all of Ill.

[73] Assignee: UOP LLC, Des Plaines, Ill.

[21] Appl. No.: 09/035,798

[22] Filed: Mar. 6, 1998

[51] Int. Cl.⁶ .............................. C07C 51/42; C07B 53/00
[52] U.S. Cl. ............................................. 562/608; 562/606
[58] Field of Search ...................................... 562/608, 606

[56] References Cited

U.S. PATENT DOCUMENTS

| | | | |
|---|---|---|---|
| 3,634,531 | 1/1972 | Platz et al. | 260/669 |
| 3,658,467 | 4/1972 | Maeck | 23/25 |
| 3,702,886 | 11/1972 | Argauer et al. | 423/328 |
| 4,088,737 | 5/1978 | Thomas et al. | 423/240 |
| 4,615,806 | 10/1986 | Hilton | 210/690 |
| 4,735,786 | 4/1988 | Inoue et al. | 423/240 |
| 4,913,850 | 4/1990 | Puppe et al. | 252/630 |
| 5,075,084 | 12/1991 | Wilhelm et al. | 423/241 |
| 5,576,458 | 11/1996 | Minami et al. | 562/519 |

*Primary Examiner*—Samuel Barts
*Assistant Examiner*—Rosalynd Keys
*Attorney, Agent, or Firm*—Thomas K. McBride; Frank S. Molinaro

[57] ABSTRACT

A solution is provided to the long sought inorganic alternative to resin based adsorbents for iodide clean-up service for corrosive organic liquid. The solution involves the use of a solid inorganic adsorbent comprising a combination of a silica-rich zeolite molecular sieve, which has been cation-exchanged with an iodide-reactive metal selected from silver, mercury, copper, lead, thallium, palladium or mixtures thereof, with a substantially insoluble, porous refractory inorganic oxide binder. Reactivation and regeneration technique for the spent inorganic adsorbent are also covered.

20 Claims, No Drawings

METHOD FOR TREATING AN ORGANIC LIQUID CONTAMINATED WITH AN IODIDE COMPOUND

FIELD OF THE INVENTION

The present invention relates to a novel method for treating an organic feed liquid contaminated with detrimental amounts of one or more iodide compounds utilizing a solid inorganic adsorbent material having the capability of removing the detrimental compounds over a broad concentration of these contaminants in the liquid stream to be treated. This invention more particularly relates to the use of an inorganic adsorbent, comprising a bound silica-rich molecular sieve which has been cation-exchanged with a metal selected from the group consisting of silver, mercury, copper, lead, thallium, palladium or mixture thereof, in the selective removal of detrimental iodide compounds such as alkyl iodide materials from corrosive and hazardous organic liquids which are customarily produced utilizing catalytic technology involving iodide co-promoters.

BACKGROUND OF THE INVENTION

In the chemical industry iodide and/or iodide compounds have been proposed in numerous applications for use as catalyst and/or catalytic promoters or co-promoters for the production of numerous higher value organic materials from lower valued organic materials. For example, in U.S. Pat. No. 3,634,531, a process for the oxydehyrogenation of ethylbenzene to styrene utilizing an iodine or bromine catalyst is disclosed. According to the specification the principal problem associated with this route to styrene is the presence of 30–50 wt. ppm of iodide in the form of organic iodide compounds in the crude styrene product. It is furthermore observed that the crude styrene product is contaminated with detrimental amounts of these iodide compounds to the extent that when they are subsequently polymerized or co-polymerized discolored products are formed which are not acceptable commercially. In addition, it is noted that the trace amounts of alkyl iodide contaminants in the crude styrene caused deactivation of catalysts in the subsequent polymerization processing steps. Attempts to separate these contaminated iodide compounds from the crude styrene by fractionation have been unsuccessful primarily because the iodide compounds are unstable and split off from the heavy materials from the bottom of the column and form detrimental amounts of iodine which are carried into the overhead product of the column and thereby contaminate the styrene once again by further reaction therewith to once again reform alkyl iodide compounds.

U.S. Pat. No. 3,658,467 addresses the problem of removing iodide compounds from gaseous streams associated with a normal or abnormal operation of atomic energy reactors. In particular, the problem addressed by the '467 patent is the removal of radioactive iodide-containing materials from the reactor environment either during the normal reactor operations or in the event of a fuel element cladding failure whereby radioactive methyl iodides are formed in significant amounts. According to the teachings of this '467 patent the removal of radioactive amounts of iodine gas has been adequately solved by means of the use of carbon filters coated with metals that react with iodine. In particular, charcoal impregnated with silver and/or copper are suggested in the teachings but it is pointed out that although charcoal absorbs elemental iodine at relatively low temperatures it is not particularly selected for the adsorption of organic iodide compounds. The solution proposed in this '467 patent is the use of a zeolite X molecular sieve exchanged with silver operated under gas phase conditions. In contrast, the present invention utilizes liquid-phase conditions and avoids the use of zeolite X in view of the fact that it is a low silica-containing material typically containing only up to 3 moles of silica per mole of alumina in its framework and thus susceptible to attack in organic media such as acidic acid that tends to react with the alumina portion of the framework X zeolite.

In U.S. Pat. No. 4,735,786, another solution to the problem of removing iodine and organic iodide-containing compounds is set forth, but once again, it is focused specifically on the problems associated with radioactive iodide compound discharge from nuclear facilities operated under normal or abnormal conditions. The '786 patent recognizes the deficiencies of the silver-exchange zeolite X adsorbent used in the prior art for gaseous phase adsorption of iodide compounds and points out that under high humidity conditions the capacity of the adsorbent is significantly reduced. The solution taught by the '786 patent is to switch to a different type of zeolite which is characterized as a high silica to alumina pentasil zeolite which has a specified molecular formula. It is well known, of course, that these pentasil zeolites are well represented by the ZSM-5 type of zeolites. As is clearly shown in U.S. Pat. No. 3,702,886 these pentasil zeolites are well known to be of medium pore consideration having pores made up of ten member rings that have dimensions in the range of 5.1 to 5.6 Angstroms. This '786 patent is however silent as to a use of the zeolitic adsorbent disclosed therein in liquid-phase treating of organic streams that have corrosive properties and also fails to suggest a use of large pore (i.e. having 12 member ring openings) silica-rich to alumina zeolitic materials for this service. In addition, the teachings of the '786 patent are focused only on separation of methyl iodide from a gas stream as is clearly shown in the results reported in the examples. As such it fails to suggest any solution to the more difficult problem of removing higher molecular weight alkyl iodides such as the $C_6$ alkyl iodide material from a corrosive liquid such as acetic acid that is of particular interest to the present invention.

In U.S. Pat. No. 4,913,850, the problem of methyl iodide removal from gaseous stream is further elaborated on and a solution is proposed in which a so called "binderless" zeolite material is utilized which is made up primarily of 80–90% zeolite X and 10–20% zeolite A. Once again however the teachings of the '850 patent teach away from utilizing a silica-rich and preferably large pore zeolite in bound form for liquid-phase treatment of corrosive organic liquids that contain alkyl iodide and other materials of molecular weight much beyond methyl iodide, as is shown in the Example, neither zeolite X or zeolite A performs in an acceptable manner in this liquid phase service.

In U.S. Pat. No. 5,075,084, the progress of the technology for cleaning up gaseous streams containing radioactive methyl iodide is continued by focusing on the unexpected and detrimental recombination reaction that can be induced by the silver-exchange zeolitic adsorbent that is proposed to be used therein. The particular problem addressed and solved in the '084 patent is, more specifically, the problem of the silver-exchanged zeolite material catalyzing the recombination reaction of hydrogen and oxygen which is very exothermic and can cause undesired catalytic ignition of hydrogen with resulting detrimental consequences to the building containing the atomic reactor. According to the '084 patent this undesired side reaction is suppressed by adding a heavy metal such as lead to the silver exchange adsorbent in order to inhibit this side reaction which can cause an exotherm in the pure silver-exchange zeolite as is clearly shown in Example 3. This '084 patent is not particularly enlightening on any of the problems addressed by the present invention and once again fails to point to a silica-rich zeolite for use in clean-up of a corrosive liquid organic medium and only suggests a mixture of zeolite X and zeolite A for use as the adsorbent both of which, as is demonstrated in the Examples, are not acceptable for use in the present invention.

In U.S. Pat. No. 4,088,737, the problem of removal of radioactive methyl iodide from a gas stream is further addressed in a multi-step treatment procedures wherein the initial gas purification treatment step is with a silver-exchanged zeolite exemplified by zeolite X. After iodide breakthrough, the regeneration and concentration steps involves withdrawing the iodide loaded adsorbent from contact with the gaseous, subjecting it to desorption conditions with an $H_2$-rich stream to produce a hydrogen-iodide containing off-gas stream and treatment of the iodide-containing off gas stream with a lead exchanged zeolite to concentrate the desorbed hydrogen iodide. Lead exchanged X is specifically exemplified. The advantage of the multi-step treatment is that the storage of the contaminated material is less expensive in a lead exchanged zeolite. Once again the teachings of the '737 patent are not relevant to the solution to the problem addressed by the present inventors in that the medium to be treated as a gas stream and the material utilized in the treatment is a low silica to alumina X-type of zeolite which has not performed satisfactorily in the corrosive environment typically faced by the present invention.

In U.S. Pat. No. 4,615,806, the particular problem of interest to the present invention is well defined in that a corrosive organic, non-aqueous liquid medium is contaminated with undesired quantities of alkyl iodides and is subjected to treatment in the liquid-phase to remove substantially all of the undesired iodide contaminants. As is explained in the teachings of this '806 patent the principal area of concern here is in the manufacture of carboxylic acids such as acetic acid via a process that results in a product stream contaminated with small amounts of iodide compounds such as methyl iodide, sodium iodide, hydrogen iodide and hexyl iodide. These organic iodide contaminants are known to cause processing difficulties in subsequent chemical conversion operations and may contaminate other materials to which the contaminated acetic acid stream is added. After reviewing the prior art on iodide contaminant clean-up the '806 patent focused on using a special type of an organic resin as an adsorbent in solving the problem and in fact taught away from the use of inorganic material of an adsorbent in its Example III. The amount of iodide contaminant in the acetic acid feed stream subjected to clean-up procedure of the '806 patent is indicated as usually between 1 ppb (i.e. part per billion) up to 100 ppb.

Except for the teachings of U.S. Pat. No. 4,615,806, the problem of removing detrimental organic iodide compounds from liquid solutions is unfortunately not as well developed as that associated with removal of these materials from gas streams. The specific prior art associated with removing organic iodides from aqueous or organic liquid solutions is well summarized in U.S. Pat. No. 4,615,806 which points to prior art teachings associated with the use of "gel-type" resins exchanged with iodide-reactive metals such as silver is acknowledged and distinguished. In this '806 patent a new method for removing organic iodides from organic solutions is taught which essentially relies for novelty on the concept of using a macroreticulated strong acid cation-exchange resin which is "stable" in the organic medium that bears the organic iodide compound to be removed and furthermore has at least one percent of its active sites converted to silver or mercury presumably by cation-exchange. The use of macroreticulated resins is stated in this '806 patent as being an advance over the prior art which are generally characterized as gel-type ion-exchange resins. While the invention of the '806 patent has been practiced commercially with some success it suffers from the fact that the resin is essentially an organic material that is known to "swell" or change dimensions (i.e. up to 50% change is permitted) when exposed to an organic medium making adsorbent bed design difficult. It is also vulnerable to decomposition at relatively mild conditions and furthermore is susceptible to chemical attack by the reagents in the corrosive organic liquid that is frequently found to be the vehicle in which the contaminated organic iodide is dissolved. Another disadvantage associated with the use of resins as an adsorbent for removing iodide-containing materials from organic solutions is the fact that the operating temperature for these materials is limited by the temperature at which the resins starts to decompose or undergoes detrimental structural changes due to softening and loss of strength associated with exposure to high temperatures. Typically, resins begin to decompose at relatively low temperatures of approximately 100–200° C. via mechanisms that are associated with destruction of the fundamental network associated with the resin as well as the cation-exchange sites. For example, the resin preferably utilized in the '806 patent is a "strong acid" cation-exchange type of resin which is essentially constructed out of a sulfonated copolymer of styrene and divinylbenzene. At relatively low temperature conditions the acid-exchange sites on this type of resin are well known to be susceptible to an acid catalyzed desulfonation reaction which can result in the release of metal cations into the effluent from the treatment step as well as detrimental sulfur-containing compounds. These materials in turn can interfere with downstream reactions in which the effluent from the iodide-treating step is used for further chemical processing. A careful reading of the '806 patent has not revealed any regeneration or reactivation mechanism taught therein primarily because these steps undoubtedly would have to be performed at relatively high temperatures that the macroreticulated resin taught therein cannot stand without substantial degradation.

The problem therefore addressed by the present invention is to provide an inorganic adsorbent for use in the treatment service specified in the '806 patent which inorganic material will be free of the substantial temperature restrictions, chemical exposure restrictions and physical swelling problems associated with the typical organic materials used in the prior art.

There are significant teachings in the prior art associated with the use of zeolitic-type adsorbents that point away from their utility in this treatment service. In particular, reference may be had to the comparative example recited in U.S. Pat. No. 4,615,806 (at column 6, line 36 through line 49) where a silver-exchanged zeolite, characterized as 1/16 inch Linde 5A pellets, was tested in iodide compound removal service from a corrosive acetic acid liquid stream and found to be unstable in that silver leached from the adsorbent continuously throughout the run and a yellowish precipitate was found in the treated effluent. Given this discouraging result with a zeolitic materials it is indeed remarkable that we have now found that a suitable inorganic adsorbent for use in this corrosive environment, which is accurately described in the '806 patent, is in fact a zeolitic molecular sieve that has been exchanged with a suitable cation material that is known to react with iodide and iodide-containing compounds at relatively mild conditions provided that the zeolitic material is a silica-rich material which is bound with a substantially insoluble binder material. Our findings are, more specifically, associated with the fact that we have now discerned that a suitable inorganic solution to the problem articulated above is the use of an adsorbent containing a zeolitic molecular sieve having a silica to alumina ratio above the point where decomposition of the zeolite is observed to occur in the corrosive organic liquid being treated. By referring to the silica to alumina ratio associated with the zeolite it is of course intended to refer to the framework silica to alumina ratio which is characteristic of the fundamental three dimensional structure which characterizes the zeolite. We have further found that the framework silica to alumina ratio which enables zeolites to perform satisfactorily in this iodide removal surface in a corrosive organic environment such as the presence of acetic acid is not a strong function of the type of zeolite but is rather largely dependent just on the framework ratio provided that it is high enough. In short, we have found good results with framework ratios above about 5:1 with better results found at a silica to alumina ratio of 6.5:1 and with superior results found at a framework ratio of silica to alumina ratio of 8:1. We have unexpectedly found moreover, that such a silica-rich zeolitic adsorbent can be reactivated via a relatively simple procedure and also regenerated at high temperatures when needed.

SUMMARY OF THE INVENTION

In general then the present invention is based on the discovery that zeolitic molecular sieves are capable of removing organic iodide-containing compounds from corrosive organic solutions such as those associated with acidic acid manufacture provided the silica to alumina framework ratio is set at a high enough ratio to prevent leaching of detrimental quantities of alumina into the effluent stream. It is thus an object of the present invention to provide an inorganic adsorbent that is stable to a corrosive environment for use in the purification of organic streams that have been contaminated with detrimental amounts of iodine or iodide-containing compounds. A second object of the present invention is to provide a method for reactivating zeolitic adsorbents that have been used in iodide compound removal service. Still another object is to provide an organic iodide-selective adsorbent that is stable to corrosive environments ordinarily associated with the organic solutions that are manufactured utilizing iodide promoters in the organic chemical industry. Still another object is to provide not only an inorganic iodide-selective adsorbent material that can stand up to the corrosive environment associated with the iodide contaminated organic streams found in the chemical industry but also an inorganic adsorbent that can be regenerated by high temperature treatment designed to decompose the silver iodide materials that are believed are formed due to the adsorption or chemisorption step utilizing a high temperature desorption stream in order to remove the detrimental iodide material therefrom typically in the form of hydrogen iodide.

In one embodiment the present invention is a method for treating an acidic organic feed liquid contaminated with detrimental amounts of one or more organic or inorganic iodide compounds which essentially involves contacting the feed stream with a solid inorganic adsorbent at adsorption conditions effective to adsorb iodide compounds and to maintain liquid-phase conditions thereby producing a substantially iodide compound free treated acidic organic liquid. The inorganic adsorbent that is utilized in this embodiment is characterized as a combination of a silica-rich zeolitic molecular sieve, which has been cation-exchanged with an iodide reactive metal such as silver, mercury, copper, lead, thallium, palladium or mixtures thereof, with an organic liquid insoluble porous refractory inorganic oxide binder. The inorganic adsorbent is used in bound form in order to provide particle sizes that are suitable for use in fixed-bed systems where pressure drop considerations necessitate the use of relatively large size materials.

In a preferred embodiment the zeolitic molecular sieve utilized in the inorganic adsorbent is a large pore zeolite (i.e. 0.6 to 0.8 nanometer) selected from the group consisting of steam stabilized Y zeolite, LZ-210, Y85 and mixtures thereof having a silica to alumina framework mole ratio greater than about 5:1.

In an especially preferred embodiment the present invention is a method for treating an acidic organic feed liquid with an inorganic adsorbent as described above wherein the solid inorganic adsorbent comprises a combination of a hydrophobic, ultra stable zeolite LZ-210 cation-exchanged with silver and having a silica to alumina mole ratio of greater than 8:1 with a silica, zirconia or titania binder in amounts such that the zeolite is at least about 70 wt. % of the adsorbent and wherein the exchanged silver is sufficient to provide one to 15 wt. % of the adsorbent on an elemental silver basis.

In another aspect the instant invention is a combination of the adsorption step described above with a reactivation step which is performed on the spent adsorbent either after break-through occurs or is about to occur. The reactivation step essentially involves withdrawing the spent adsorbent from contact with the organic feed liquid and thereafter contacting the withdrawn adsorbent with a solution of a salt of silver, mercury, copper, lead, thallium, palladium or mixture thereof under ion-exchange conditions until an additional increment of such metal is incorporated therein by ion-exchange.

According to yet another embodiment of the present invention the spent solid adsorbent recovered from the iodide adsorption step recited in the first embodiment is subjected to regeneration by treating with a gas stream containing hydrogen or a mixture of hydrogen with an inert gas thereof at regeneration conditions, including a temperature of about 350 to 600° C., to produce a hydrogen iodide-containing gaseous effluent stream and an iodide-depleted solid adsorbent suitable for reuse in the adsorption step after it is treated to restore the iodide-reactive metal contained therein to the active state.

Other objectives and embodiments are associated with the various preferred procedures and features connected with the instant invention discussed in the following detailed description thereof.

DETAILED DESCRIPTION OF THE INVENTION

The feed for the process of the present invention can be broadly any organic material that is contaminated with one or more detrimental organic iodide compounds. Typically, these organic feeds are produced in industrial processes that utilize iodide or inorganic or organic compounds of iodine to promote or catalyze the particular synthesis reaction carried out in the industrial process. As was pointed out hereinbefore the use of organic iodide compounds as promoters in various reactions has been widely disclosed in the literature particularly their use in the oxydehydrogenation of various organic materials to make the corresponding unsaturated compounds. A particular use of utmost concern to the present invention is associated with the well known technology for using organic iodide compounds as a promoter or co-promotor for the catalytic carbonylation of alcohols to make the corresponding carboxylic acids. The background associated with the use of alkyl iodides as promoters or co-promotors for the synthesis of organic carboxylic acids is discussed in U.S. Pat. No. 5,576,458 and in detail and will not be repeated here. In the case of most interest associated with the instant invention methyl iodide is used as a co-promoter in the synthesis of acetic acid from methanol using carbon monoxide as the carbonylation agent. Typically, it is preferred to use the instant invention for clean up of iodide contamination in organic carboxcyclic acids having 2–5 carbon atoms such as acetic, proprionic, butyric and valeric acids. The organic iodide present in the organic solution is typically an alkyl iodide having from 1–10 carbon atoms therein. Even though methyl iodide may be used as the promoter in the synthesis reaction nevertheless other alkyl iodides are generated during the course of the reaction as by-products and tend to find their way into the product stream as contaminants therein. Some of the lower boiling organic and inorganic iodide compounds can be removed from the product carboxylic acid stream via a simple technique such as distillation which is customarily used in working up the product from an organic acid synthesis plant. In the case of most interest to the present invention the detrimental alkyl iodides will be concentrated in the $C_1$ to $C_7$ range primarily because these will co-boil to some extent with the carboxylic acid stream that is subjected to a preliminary purification step via distillation. The amount of the alkyl iodides present in the streams to be treated by the instant invention can range from about 10 to about 1,000 ppb with a more typical stream having an alkyl iodide concentration equivalent to less than about 100 ppb iodide calculated on an elemental basis. The feed stream may also contain significant amounts of water due to the presence of water in the synthesis medium that produced the stream to be purified by the method of the invention. Typically, water can be present in amounts ranging from 10 ppm up to the solubility limit of water in the organic medium of interest. In the case of the feed stream being derived from the synthesis of acetic acid it is expected that the amount of water contained therein will be about 50 to 5000 wt. ppm of water with the ordinary commercially-produced material expected to have approximately 1000 wt. ppm of water in the typical mode of operation. We believe that our clean up treating technology works best when the amount of water is held to a level in the range of 1 to 1000 wt. ppm with a preference towards 5 to 500 wt. ppm. In some circumstances, it is within the scope of the instant invention to take well known steps to dry the feed to achieve water levels in the desired range. With respect to other contaminants that may be present in the feed it is best practice to minimize these and we believe that appropriate steps should be taken to exclude from the feed materials such as various aldehyde and ketone contaminants that are known to have the capability to reduce iodide-reactive metals ions (e.g. silver cations). The elemental state for the exchanged metal in the adsorbent is believed to be less active for the instant adsorption service and the presence of these reducing agents in the feed is not recommended. Although the instant invention is focused on the problem of removing organic iodide compounds from corrosive organic streams this is not designed to exclude the possibility that there may well be some inorganic iodide compounds present in the feed stream such as hydrogen iodide and various inorganic salts of iodide. These last materials will be typically present if at all in very small amounts and they also will be absorbed by the instant iodide clean up technology. As is noted in the teachings of U.S. Pat. No. 4,615,806 the most difficult iodide compound to remove from acetic acid solutions is believed to be hexyl iodide which is thought to normally fractionate into the final acetic acid product.

Still another factor that enters into the feed stream definition is the question of the pH of same. In most cases when dealing with organic carboxylic acids that have been contaminated with iodide compounds the pH of the organic solution will be in the range of about 2.5 to about 5. This low pH condition is believed to be the principal reason why the prior art has failed to come up with an inorganic adsorbent for use in cleaning up of this type of stream. It is an essential feature that the iodide purification technology of the present invention is capable of working on a low pH organic liquid without producing additional contamination of the treated organic stream.

In the case where the organic feed stream to the present process contains hydrogen iodide and/or other inorganic iodide compounds in amounts in excess of 100 wt. ppb, expressed as elemental iodide, it is within the scope of the instant invention to subject the feed stream to an optional pretreatment step designed to eliminate these excessive amounts of inorganic iodide compounds. In the teachings of U.S. Pat. No. 5,576,458 a pre-purification step is taught in the last full paragraph of column 9 and involves the use of a selective reaction (i.e. $CH_3OH+HI \rightarrow CH_3I+H_2O$) to eliminate undesired amounts of inorganic or organic iodide compounds and in particular undesired amounts of hydrogen iodide. According to this prior art teaching the feed stream containing excessive amounts of iodide compounds is contacted in a distillation column with sufficient amounts of methanol to enable the reaction between methanol and hydrogen iodide to proceed to produce methyl iodide plus water. This inorganic reaction is performed at conditions well known to those skilled in the art in a distillation column operated such that the products methyl iodide and water are removed overhead from the column and an organic stream containing less than 100 ppb of hydrogen iodide is removed from the bottom of the column. In many embodiments of the present invention it is distinctly advantageous to recycle the resulting methyl iodide containing overhead stream to the carboxylic acid synthesis zone in order to provide an additional source of methyl iodide to the reaction zone thereby conserving on the amount of fresh methyl iodide reagent that has to be added in order to enable the synthesis reaction to proceed.

Still another type of optional pretreatment step that is within the scope of the invention is described in U.S. Pat. No. 4,615,806 at column 5, line 34, wherein the use of a carbonaceous material is utilized in a precontacting step in order to remove hydrogen iodide and any trace amounts of iodine from the feed stream prior to the iodide treatment step. Particularly effective in this service are carbonaceous materials including activated carbons, wood charcoal, bone char, lignite and the like which may or may not be impregnated with various alkali or alkane earth metal reagents that are known to increase capacity for chemisorption of inorganic iodide compounds. This pretreatment step with carbonaceous material is conducted at conditions including a reaction time sufficient to eliminate detrimental amounts of inorganic iodide compounds, particularly hydrogen iodide, from the feed stream to the treatment procedure of the present invention in order to conserve reaction sites for use in adsorption or chemisorption of organic iodides. It is, of course, within the scope of the present invention to combine both the HI reaction pretreatment step with the carbonaceous material precontacting step. This particular combination treatment procedure can be in general done in any order but it is definitely preferable to first react the excessive hydrogen iodide with methanol and then finish up with the carbonaceous material treatment in order to prepare a stream that is charged to the organic iodide treatment procedure of the present invention and contains substantially less than 100 wt. ppb of iodide compounds and preferably less than 50 wt. ppb iodide compounds, calculated on an elemental iodine basis.

In accordance with the present invention the resulting organic liquid feed stream containing undesired amounts of organic iodide compounds is contacted with an inorganic adsorbent comprising a combination of a silica-rich zeolitic molecular sieve, which has been cation exchanged with a metal that is reactive with organic iodide compounds and is typically used in the form of a pellet, pill or extrudate which utilizes a substantially insoluble (i.e. in the organic stream to be treated) porous refractory oxide material as a binder. This contacting with the inorganic adsorbent of the present invention is performed at reaction/adsorption conditions which are sufficient to result in adsorption or chemisorption of the detrimental iodide compounds without adversely effecting the other organic materials that are present in the feed stream. Without the intention of being limited by this explanation we believe that the reaction mechanics of the adsorption/chemisorption reaction that occurs in the treatment step of the present invention essentially involves a reaction where the organo iodide compound decomposes into a corresponding unsaturated hydrocarbon and a molecule of hydrogen iodide which is then adsorbed on the active sites of the adsorbent material in the form of the corresponding metallic iodide. The unsaturated hydrocarbon that is produced by this decomposition reaction passes into the effluent where it forms a trace ingredient of the product stream typically present as a $C_2$ to $C_8$ olefin compound or a reaction product of an olefin with other ingredients of the feed stream.

The key ingredient of the novel inorganic adsorption material of the present invention is the silica-rich, zeolitic molecular sieve which is utilized therein. By the use of the term "silica-rich" it is meant to cover zeolites that have sufficient silica to alumina framework ratios that they will not be adversely effected by being subjected to prolonged contact with mildly acidic or corrosive organic stream that constitutes the feed stream to the present invention. This means more specifically that they will stand up to a typical feed stream comprising a low pH solution of acetic acid without releasing detrimental quantities of alumina or other ingredients into the effluent stream. A simple test for determining whether or not the "silica-rich" requirement of the instant invention is met is if the particular zeolite in question can be subjected to continual contact with a neat solution of acetic acid at a temperature of about 10 to about 200° C. for 24 hours without substantial dissolution of the framework alumina in the zeolite. This dissolved alumina typically manifests itself as a cloudy precipitate found in the effluent during contact of the neat acetic solution with the zeolite material. We have found very good results utilizing zeolites that have a framework ratio of silica to alumina of greater than 5:1 with best results obtained when this ratio is above 8:1. It is, of course, possible that to prepare the desired "silica-rich" zeolite in situ by first subjecting the zeolitic material to an exposure to the feed stream for a sufficient period of time to leach out sufficient alumina to stabilize the system versus the acidic environment of the feed stream; however, this type of procedure is not a preferred embodiment of the instant invention. This last in situ treatment, of course, has to be conducted in such a manner that there is a zeolitic activity for cation exchange with iodide-reactive metals present when the material has been leached to the point where it is stable to further exposure to the acetic feed stream.

With respect to the type of zeolitic material useful in the instant invention it is well known that for purposes of adsorption activity there are essentially three broad classifications of zeolite which are ranked according to the number of tetrahedral molecules that are linked together to form the pore openings that are defined by either 8,10 or 12 tetrahedral building block units linked together to form 8,10 or 12 member ring openings. Useful zeolites for the present invention included within the 12 member ring classification is the type Y faujasite structures, mordenite, type L, omega, ZSM-12 and beta. Useful zeolites within the 10 member ring pore size classification are ZSM-5, ZSM-11, ferrierite, ZSM-23 and some silicalite materials containing small but significant quantities of alumina. It is to be particularly noted that type A (as defined in U.S. Pat. No. 2,882,243) molecular sieve which contains apertures having 8 member rings is not included within the scope of the invention primarily because it is not ordinarily available in a silica-rich version. Likewise, it is to be carefully noted that type X molecular sieve is not within the scope of the present invention because it is an alumina-rich material that cannot be made into a silica-rich material which will stand up to an acidic environment. ZSM-5 is defined in U.S. Pat. No. 3,702,886 and referenced thereto may be had for its synthesis details. ZSM-11 is defined in U.S. Pat. No. 3,709,979 and reference may be had thereto for its synthesis details. ZSM-23 is defined in U.S. Pat. No. 4,076,842 and reference may be had thereto for synthesis details. Silicalite is defined in U.S. Pat. No. 4,061,724 and referenced thereto may be had for further details. With respect to type Y zeolites that are useful in the present invention these are broadly defined in U.S. Pat. No. 3,130,007 and reference may be had thereto for synthesis and structural details. Mordenite is a naturally occurring silicious zeolite which has both 12 ring pores and 8 ring pores but the 12 ring pores are the ones primarily of interest to the present invention. The structure and properties of mordenite zeolite are described in *Zeolite Molecular Sieves* by Donald W. Breck (John Wiley and Sons, 1974) at pages 122–124 and again at pages 162–163 which may be referred to for further information on this structure and synthesis of this material. Zeolite L is defined in U.S. Pat. No. 3,216,789 and reference thereto may be had for information on its unique structure as well as its synthesis details. Zeolite omega is defined in U.S. Pat. No. 4,241,036 and further details with respect to its structure, composition and method of synthesis may be had by referring thereto. With respect to zeolite ZSM-12 the key characterization patent is U.S. Pat. No. 3,832,449 which can be referred to for additional details related to its structure, composition and method of synthesis. Zeolite beta is defined in U.S. Pat. No. 3,308,069 and reference may be had thereto for additional information with respect to its structure, composition and preferred methods of synthesis. Considering all of such silica-rich zeolitic materials having 10 to 12 member ring pore openings we much prefer to utilize those having the Y zeolite structure that have been modified to achieve the high silica to alumina framework ratio required by the present invention. In the present invention case this ratio is greater than 5:1 and in the especially preferred cases it is greater than 8:1. Particularly preferred are type Y zeolites that have been modified either by steam stabilization, chemical treatment or a combination of both of these types of modifications. Steam stabilization of a Y zeolite normally involves calcination of the ammonia or hydrogen form of a Y zeolite starting material at relatively high temperatures typically above 500° C. in the presence of steam. Typically this steam calcination procedure is then followed by one or more additional ammonia ion-exchange procedures followed by additional steam calcination treatments until the sodium content of the resulting zeolite is dropped to levels corresponding to less than 0.5 wt % sodium, calculated as sodium oxide. U.S. Pat. No. 3,929,672 can be referred to for additional details with respect to a preferred steam-stabilized Y zeolite of utility in the present invention. A second type of modified Y zeolite that is of interest in the present invention is the so called LZ-210 version which depends on chemical treatment in order to increase the silica to alumina framework ratio in the zeolite by selectively replacing alumina tetrahedral units with silica tetrahedral units via so called secondary synthesis technology. Zeolite LZ-210 is defined in U.S. Pat. No. 4,503,023 and reference may be had thereto for additional information with respect to its synthesis from conventional Y zeolite by chemical treatment. Preferred LZ-210 zeolites for use in the present invention have silica to alumina ratios of about 5 to about 20. The last type of modified Y zeolites that is particularly useful in the instant invention are characterized as Y-85 which is a steam stabilized and chemically modified zeolite Y the preparation of which is fully disclosed in U.S. Pat. No. 5,013,699 and reference may be had thereto for further details with respect to its synthesis. Even though the preferred zeolitic material for use in the present invention is a chemically and/or steam modified zeolite Y material it is the best mode of practice to utilize LZ-210 type of materials since they have been found to give the best results. Within the class of LZ-210 type of materials it is preferred to use a material that has a silica to alumina framework ratio of at least 5:1 with best results obtained with a silica to alumina framework ratio of greater than 8:1. LZ-210 zeolite is thus the type of hydrophobic, ultrastable, zeolitic material that is most suitable for use in the present invention.

The silica-rich zeolitic molecular sieve utilized in the present invention must be activated by suitable ion-exchange with any metallic material known to be a reactive with alkyl iodides. We have found that ion exchange with a salt of silver, mercury, copper, lead, thallium, palladium or mixtures thereof gives good results in this alkyl iodide chemisorption and/or adsorption service. The method of converting the sodium, ammonia or hydrogen ion-containing molecular sieve starting material described above into the active form suitable for use in the present invention is well known to those skilled in the art. Any water soluble salt of the metals recited above can be utilized in an ion-exchange procedure provided the salt chosen is sufficiently soluble in water. It is, of course, well known that a non-aqueous organic medium can also be used if sufficient solubility of the salt can be achieved. Acetate, nitrate or halide salts are ordinarily utilized in the ion-exchange procedure in order to facilitate introduction of the desired metallic cation into the molecular sieve. Typically the ion-exchange procedure is performed by contacting the unexchanged molecular sieve with a suitable solution of the metallic salt to be exchanged into the sieve at appropriate cation exchange conditions which are typically room temperature and atmosphere pressure. This offering of cation-rich solutions to the molecular sieve is repeated a sufficient number of times if necessary to achieve the desired loading of the cation material. In some cases it may be advantageous to dry and calcine the material between ion-exchange treatments in order to achieve a higher level of penetration of the desired cation into the molecular sieve material. After the ion-exchange step it is a preferred practice to dry the exchanged material at 70 to 400° C. for several hours in order to remove the ion-exchange solution and activate the zeolite. We typically prefer loading of the zeolitic molecular sieve with sufficient cation to achieve an adsorbent that has about 1 to about 15 wt % of the cation exchanged material present therein as the metallic cation, calculated on an elemental basis. Best results are ordinarily achieved with a metal loading of about 8 to 12 wt % of the desired metallic cation on the adsorbent material. For most applications of our iodide clean up technology a silver cation exchanged zeolitic material is most preferred. The necessary level of silver on the zeolitic material can be achieved typically by contacting the material with an aqueous solution of silver acetate and/or nitrate for a sufficient period to allow the zeolitic material to adsorb the necessary amount of silver cations. The resulting cation exchanged material is typically dried at a temperature of 100 to 200° C. and then is directly useable in the process of the present invention. It is to be noted that the ion-exchange procedure characterized above can be applied directly to the zeolite powder prior to its formation into large particles such as pellets or extrudates or spheres suitable for use in a packed bed system or it can be performed upon the combination of the zeolitic material with the binder that is actually used in the iodide removal service. The preferred mode of operation is to incorporate the metallic cation material in the zeolitic component of the instant adsorbent once it has been bound up into a larger size particle suitable for use in a fixed-bed system. Typically, the crystal size of the molecular sieve powder that is used in the present invention is in the range of 0.1 to 6 microns but these crystallates are typically agglomerated into powder particles having sizes in the range of 10 to 20 microns. The size of the particles that are useful in a fixed-bed system in contrast run from particles having a diameter of about 800 microns to those having a diameter of about 3200 microns or more. Typically a particle having a diameter of about 1600 microns is preferred for use in the present invention although the exact dimension of the particles is not viewed as being critical. The only requirement here is that when the particles are put in a fixed-bed system that the pressure drop across the bed is suitable for a commercial operation.

There are numerous ways described in the prior art for combining a binder material with molecular sieves in order to make the larger size particles that are suitable for the instant invention and have sufficient crush strength so that they will not break apart in the contemplated iodide purification service. The binder material is, of course, selected so that it is not soluble to any significant extent in the corrosive organic liquid that will be the feedstock to the treatment step of the present invention. We have found that best results are obtained where the binder material is selected such that it is substantially insoluble in the feed stream to be treated and by "insoluble" we mean that less than 10 ppm of the binder material is found in the effluent after an acetic acid solution has been passed over the particles of the adsorbent at iodide adsorption conditions specified herein for a period of 100 hours. This initial 100 hour period provides a reasonable period for the adsorbent material to stabilize and reach its final start of run composition.

Binder materials found to be useful in preparation of the iodide adsorbent of the present invention are alumina, silica, titania, zirconia, chromia, boria, vanadia, magnesia and mixtures thereof with best results typically achieved with a binder selected from the group consisting of silica, titania and zirconia. Alumina is not preferred and is only satisfactory for runs of short duration. The most preferred binder for use in the instant adsorbent is silica in view of its ready availability and reasonable economics associated with its use. The formation of shaped agglomerates of the silica-rich zeolitic molecular sieve and the binder material can be accomplished by any of the techniques known to the prior art. In one preferred technique the agglomerization step can be performed via an extrusion procedure in which sufficient quantities of the zeolite powder are blended with the targeted quantity of binder and the resulting mixture is blended with sufficient water and a peptizing agent to form a gel or dough which can be then extruded using technology well known to those skilled in the art. The extruded pellets formed by this procedure most commonly will have a cylinderial cross section although it is perfectly possible to form a wide variety of cross sectional shapes which lessen the gross diffusional path for the contaminants into the large pores of the adsorbent. A particularly preferred type of pellet for use in adsorption service is a trilobal material that is extruded such that it has a 3-leaf cross sectional shape. The union of the binder material with the zeolitic material can be also accomplished by the formation of spherical beads using technology that is well known in the adsorbent art. The resulting beads can be essentially spherical or they can be oblate or any other desired shape. Typically, the formation of the extrudates or the beads or pellets is performed in a forming stage which produces so called "green" particles which possess sufficient strength to be passed into a subsequent calcination step which sets the binder and activates the molecular sieve. It is to be noted that the molecular sieve can be preexchanged with the metallic ingredient as indicated above although the preferred practice is to do the exchange after the molecular sieve powder is bound up in the desired agglomerates. The firing step that converts the green particles into the final particle suitable for use in the adsorption service can be performed at a temperature sufficient to set the binder which typically ranges from 450° C. to 700° C. with 600 to 650° C. being preferred. The amount of a binder material utilized in preparing the adsorbents of the present invention is typically less than 30 wt. % of the finished product and preferably constitutes 15–25 wt. % of the product calculated as the corresponding oxide. That is the preferred adsorbent should contain at least about 70 wt. % of the zeolitic molecular sieve and more preferably contains 75 to 85 wt. % of molecular sieve. The balance of the unexchanged adsorbent then would be the binder material. The exchange of the metallic ingredient into the molecular sieve will, of course, decrease the relative proportions of the molecular sieve and the binder in the adsorbent once all three ingredients are considered.

The preferred method of formation of spherical adsorbent agglomerates that are utilized in the treatment step of the present invention is by means of the well known "oil-drop" technique. This procedure is explained in detail in U.S. Pat. No. 2,620,314 and essentially involves the formation of an appropriate sol of the binder or carrier material that is to be utilized as the matrix for suspending the active zeolitic material. In the case of the preferred binders mentioned above for the instant adsorbent material it is appropriate to make an acidic hydrosol that can be gelled using the type of temperature-activated basis gelling agent which is set forth in this '314 patent. That necessarily implies that the sol should be slightly acidic in order to be gelled by a temperature sensitive gelling agent such as the hexamethylenetetramine (HMT) that is the preferred temperature-activated gelling agent mentioned in the this patent. It is, of course, to be recognized that in the case of silica sols it is often times not necessary to use a gelling agent in order to get the sol to gel. Some of these silica sols are well known to gel merely due to a change in temperature and this type of sphere formation is within the scope of the present invention. The type of silica sol that can be used to form the silica binder are commercially available in the form of aquasols or organosols having colloidal silica particles dispersed therein. In fact, in many cases when using silica sols it is not necessary to use either a gelling agent or a substantial thermal treatment in order to convert to a sol into a suitable gel in view of the fact that the silica sol when blended with the silica-rich molecular sieve described above will set sufficiently to form a viscous mixture that can be agglomerated by controlled drying into the desired particles of the appropriate size for use in the present invention. For oil dropping with a silica sol it is preferred to use an inverted silica sol produced by methods using acid addition techniques and a basic gelling agent such as a mixture of urea and HMT. When a zirconia binder is used with the oil-drop preparations procedure the preferred acidic sol is an aqueous solution of zirconyl hydroxylchloride and urea. When a titania binder is used with this oil-drop procedure the acidic sol is preferably a solution of titanyl oxychloride and urea.

The important feature of all of these well known techniques for forming agglomerates of the binder and the silica-rich molecular sieve is that the interaction with the binder be conducted in such a manner that the particles of the sol do not block the pores of the molecular sieve to any significant degree. As is well known this phenomenon is called "binder blinding" and can cause interference by the binder with access of the organic iodide compounds to the active sites in the molecular sieve. In some cases it may be necessary to add to the mixture of molecular sieve and binder prior to agglomerate formation an inert diluent material which is typically of somewhat smaller size than the molecular sieve powder which diluent can act as a bridging material for interacting with the binder and thus preserving the pore system of the zeolite. Typical inert diluents for use as additives to prevent binder blinding are non-colloidal silica's and some species of clays that are resistant to low pH conditions. An essential feature of the present invention is, of course, then in all cases the chemical characteristics of the binder are matched with the silica-rich molecular sieve and the corrosive nature of the organic solution to be treated such that both the molecular sieve and the binder material are substantially insoluble in the acidic organic stream to be treated as was explained in detail hereinbefore. Regardless of specific method of agglomerate formation, the resulting particles will in all cases be dried at a relatively low temperature at 80 to 150° C. for several hours and then calcined in dry air at about 450 to 750° C. with 600 to 650° C. being preferred in most cases.

According to the present invention then the organic liquid stream containing the iodide contaminates is contacted with an adsorbent comprising a combination of silica-rich zeolitic molecular sieve containing metallic cation that are reactive with alkyl iodide with a substantially insoluble porous refractory inorganic oxide binder selected as explained above. It is a preferred practice that the active metal that is reacted with the iodide-containing organic materials is added to the resulting adsorbent particles after their formation in order to avoid possible loses of valuable metallic ingredients during the formation of the agglomerated material. As explained above the preferred practice is to cation exchange the active sites in the molecular sieve with a soluble salt of silver, mercury, copper, lead, thallium, palladium or in some cases a mixture of one or more of the salts of these metals. As is well known to those skilled in the art this cation exchange procedure is usually conducted at room temperature and atmospheric conditions and the driving force for completion of the exchange is the concentration gradient of the metallic ingredient from the solution into the material possessing the cation exchanged sites. It is also a well known procedure to perform this cation exchange step multiple times in order to build up the desired concentration of the metallic ingredient in the adsorbent. Once the desired quantity of metallic ingredient is incorporated in the agglomerate the resulting adsorbent is then subjected to a drying step at a temperature of about 100–300° C. for several hours and thereafter can be subjected to an optional calcination step in order to fix and activate the adsorbent in its final form. The optional calcination step can be conducted with dry air at temperatures of 400 to about 700° C. for several hours if careful attention is paid to the crystal structure of the silica-rich zeolitic material to ensure that no substantial amount of the crystal structure is destroyed by the exposure to the high temperature conditions and if its temperature is chosen so that the exchanged metallic cations in the silica-rich molecular sieve are not substantially disturbed. Ordinarily, it's a preferred practice to minimize or eliminate any detrimental amounts of steam from the environment of the adsorbent as it is under going the optional calcination step. That is to say that the preferred practice is to conduct both the drying step and the optional calcination step procedure without additional moisture being added to the environment of the adsorbent that is being fired and fixed.

The adsorption conditions that are preferably utilized in the iodide compound adsorption step of the present invention are well known to those skilled in the art and include a pressure sufficient to maintain the liquid-phase solution which in most cases is about 1 to 10 atmospheric (i.e. 101 to 1010 kPa) a temperature sufficient to cause appropriate interaction of the contaminants with the active sites in the adsorbent and generally includes a temperature of about 20° C. to about 350° C. with a preference for a temperature of 40–150° C. It is to be noted that a feature of the present invention is that it can operate successfully at higher temperatures than the resin based adsorbent of the prior art since its constitutes are all inorganic materials that are resistant to the degradation that ordinarily accompanies organic materials as they are exposed to high temperatures. A suitable liquid hourly space velocities ("LHSV") are selected from the range of about 0.5 to about 15 hr$^{-1}$ with a preferred range being a LHSV of about 1 to about 10 hr$^{-1}$. As is well known to those skilled in the art LHSV is determined by dividing the hourly flow rate of the liquid feed to the zone containing the adsorbent by the volume of the bed of adsorbent contained in the adsorption zone to produce a number which is inversely-proportional to residence time in the adsorbent.

It is within the scope of the instant invention to take the effluent from the adsorption zone that has been substantially depleted in concentration of detrimental iodide-containing contaminants (i.e. preferably to a level of less than 10 wt. ppb and especially to a level less than 5 wt. ppb of iodide, calculated on an elemental iodine basis) and pass this effluent over a second bed of the silica-rich zeolitic molecular sieve containing adsorbent which has not been cation exchanged with an iodide reactive metal (i.e. the unexchanged form) and which bed would act as a guard bed to recover or "trap" any of the metallic cations that had been present in the iodide adsorbent during the iodide removal step and were released into the effluent due to displacement by the hydrogen ion in the acetic acid during the adsorption or the chemisorption step. This procedure will ensure that any active cationic metals released from the adsorbent during the adsorption step are trapped and retained within the system and do not contaminant the final product stream. Although it is possible to use the unexchanged organic adsorbents of the prior art in this service (especially the macroreticulated strong-acid cation exchange resin material disclosed in U.S. Pat. No. 4,615,806 in an unexchanged form) we prefer to use the unexchanged form of the inorganic adsorbent of the present invention. It is, of course, within the scope of the present invention to periodically reverse the flow through the two bed system in order to push an active mass transfer zone containing the metallic cations that are reactive with iodide from one bed to the other thereby making them continually available to the principal reaction which involves adsorption and/or chemisorption of the organic iodides on the active exchanged metals such as silver. The details associated with the operation of such a two bed system are well known to those of skill in this art.

A surprising finding associated with the present invention is with respect to the reactivation of the spent adsorbent when it has been exposed to sufficient detrimental iodide compounds that break-through of iodide into the effluent stream is about to occur. It has now been determined that it can be reactivated by a simple re-exchange procedure. We have found that the adsorbent can be reactivated by taking it off stream and subjecting it to an additional ion-exchange step with another quantity of the iodide-reactive metallic ingredient such that at least a portion of the active metallic sites in the adsorbent are reestablished. The amount of metallic ingredient added by the ion-exchange procedure previously described in the reactivation treatment is preferably about 0.5 to 1.5 of the amount originally charged to the adsorbent when it was freshly made although this may be subject to some variation depending on the degree of deactivation of the metallic ingredient. This reactivation procedure can be repeated as shown in the Examples a number of times thereby vastly extending the active life of the iodide-selected adsorbent until more drastic measures have to be taken in order to recapture some capacity for iodide adsorption. We have had success with up to six cycles of reactivation before there was any substantial tailing off in performance of the inorganic adsorbent.

When the reactivation procedure fails to reestablish sufficient iodide removal capacity in the spent inorganic adsorbent of the present invention it is contemplated that more drastic measures can be taken in order to free the pores of the molecular sieve of detrimental metallic iodide blocking materials. In the preferred case where the metallic ingredient is silver the pore blocking materials would be silver iodide. We have observed that there is a tendency for silver iodide once formed to migrate out of the pores onto the binder and in the process block a significant number of the pores of the adsorbent but this migration is slow and does not proceed at a fast enough rate to interfere with the sieve being reactivated for at least the first 5 to 10 cycles. When the performance of the iodide selective inorganic adsorbent drops to the point where more severe regeneration is needed we have found that exposure of the inorganic material to high temperatures in the presence of a reducing agent such as hydrogen, hydrogen admixed with one or more diluent material or equivalent reducing materials is beneficial. The metallic iodide loaded deactivated adsorbent is, more specifically, subjected to a high temperature treatment with a reducing agent in order to reduce silver iodide and liberate substantial quantities of hydrogen iodide. As is explained in U.S. Pat. No. 4,088,737 this type of regeneration procedure requires a moderate pressure of about 1 to 10 atmospheres a high temperature of about 400–550° C. and a gas hourly space velocity (GHSV) of about 400 to 1000 $hr^{-1}$. This treatment liberates a gas stream containing hydrogen iodide which can be returned to the process that utilized the iodide reactant in order to synthesize, for example, acetic acid or it can as explained above be further reacted with methanol in order to make methyl iodide which can be utilized as the principal reagent in the upstream chemical synthesis step. Once the hydrogen iodide is stripped off the spent adsorbent then appropriate steps can be taken to oxidize the metallic reagent which remains in the adsorbent and return it to a cationic state where it can be reused in activating the iodide selected adsorbent of the instant invention. The techniques that can be utilized to oxidize metallic ingredients to cationic form and to reexchange the resulting cations with the active sites of the silica-rich molecular sieve are well known to those who are skilled in the art.

In some cases where the iodide adsorption step of the present invention is applied to an extremely corrosive organic stream it is possible that some small amounts of silica and/or alumina may be leached from the molecular sieve which is the active ingredient in the adsorbent until the silica to alumina framework ratio is increased to a level such that it is resistant to any further dissolution in the corrosive stream. During this interim or start-up period when the desired silica-rich molecular sieve of the present invention is being formed in situ it is within the scope of the present invention to use a post-treatment step to remove any detrimental amounts of soluble silica or alumina from the iodide-depleted product stream. The most preferred treatment for eliminating soluble quantities of aluminum and or silicon from the effluent stream is to pass it over a strong acid cation exchange resin such as is described in U.S. Pat. No. 4,615,806 with the exception that it is not necessary to use an ion-exchange material that contains silver or mercury in view of the fact that the iodide removal procedure has already taken place. In some cases, it may be advantageous to use any other suitable known cation exchange organic or inorganic material to accomplish the desired clean up of the effluent stream during this start-up period via techniques well known to those skilled in the art.

The adsorption step of the present invention can be performed according to any of the techniques known to those skilled in the art. Specifically, a fixed-bed system, a moving bed system, a fluidized system or a batch type of operation can be utilized. It is ordinarily preferred to use a fixed-bed system with the adsorbent continually flowing through the adsorption zone containing the active adsorbent as explained hereinbefore. It is, of course, to be understood that the adsorption step may be performed in plurality of adsorption zones with suitable means there between to ensure that the desired conditions are maintained therein. In any case best results are obtained when the adsorption conditions are adjusted to achieve an effluent stream containing less than 10 ppb of iodide, calculated on an elemental basis, and it is within the scope of the present invention to achieve iodide levels in the effluent less than 5 ppb with the best practice being to adjust conditions to achieve less than 1 ppb. With regard to mechanics of the operation of the instant invention it is, of course, possible to use any of the swing-bed systems of the prior art to alternate beds of adsorbent between the adsorption step and the reactivation and regeneration steps of the present invention.

The following examples are given for purposes of illustrating the benefits and advantages associated with the instant invention and of contrasting it with the prior art particularly in the case of prior attempts to use molecular sieve adsorbents in this type of hazardous material treatment service. While these examples are provided to illustrate the present invention they are not intended to limit it.

Comparative Example 1

The comparative example of U.S. Pat. No. 4,615,806 set forth at column 6, line 35–49, is hereby incorporated by reference. According to this comparative example an attempt was made to remove detrimental iodide compounds from a liquid solution essentially comprising pure acetic acid utilizing a 50 ml portion of a 1/16 inch (1.6 mm) particle size of 5A pellet containing unspecified amounts of zeolite A (see U.S. Pat. No. 2,882,243 for definition) which had been ion-exchanged with silver nitrate in an amount sufficient to incorporate at least some silver in the molecular sieve materials. The silica to alumina framework for zeolite A is typically 2:1. A synthetic solution of methyl iodide and acetic acid was then allowed to pass over this bed of particles of silver-exchanged 5A sieves at apparently room temperature and atmospheric pressure at an LHSV of 1 $hr^{-1}$. It was observed that silver leached continuously during the run into the effluent stream and a yellowish precipitate which was believed to be silver iodide formed in the treated acetic acid effluent stream indicating that breakthrough of the methyl iodide occurred very quickly. Performance was reported as unacceptable.

Comparative Example 2

An adsorbent comprising zeolite X as defined in U.S. Pat. No. 2,882,244, in a powder size of 0.1 to 6 microns is bound with a kaolin-type of clay to make an agglomerate having a particle size range of 150 to 840 microns. The amount of zeolite X used was sufficient to result the uncalcined adsorbent material having 80% by weight zeolite. The resulting agglomerates were dried at 75° C. for 3 hours and then calcined in dry air at a final temperature of 600° C. for 4 hours. The calcined adsorbent particles were then soaked in an aqueous solution of silver nitrate until sufficient silver had been cation exchanged with zeolite X to result in particles containing 10.5 wt. % silver in the form of exchanged silver cation. The resulting silver-exchanged particles were water washed and free of exchange solution and dried at 300° C. for 2 hours.

The resulting adsorbent had a silica/alumina framework ratio of 2.5, a silver content of 10.5 wt. % and an ABD (Apparent Bulk Density) of about 0.7 cc/g.

A breakthrough test was then performed to determine the capacity of this silver exchanged containing zeolite X-adsorbent for adsorption of methyl iodide from an acetic acid solution. The particles of the adsorbent were loaded into a 50 cc column and a feed solution containing about 500 ppm methyl iodide in acetic acid was passed there through at iodide adsorption conditions including a LHSV (i.e. liquid flow rate divided by bed volume) of 4 $hr^{-1}$, a pressure of 690 kPa and a temperature of 60° C.

Almost immediately the effluent from the test zone was found to turn cloudy and a precipitate formed. Upon analysis the precipitate was found to contain silver iodide indicating that iodide breakthrough occurred very early in the run. In addition the effluent showed substantial content of alumina indicating zeolite framework breakdown as well as binder degradation and leaching. Performance was unacceptable.

EXAMPLE 1

An adsorbent was prepared using a special type of zeolite Y known as zeolite LZ-210 (See U.S. Pat. No. 4,503,023 for definition) having a silica to alumina framework ratio of 10:1 and an alumina binder, according to the extrusion method previously described. The resulting extrudate particles were then ground and sized to a particle size of 150 to 840 microns. Analysis showed the material to be 80% zeolite and 20% binder by weight. The resulting material was dried, calcined, silver-exchanged, water washed and dried in the same manner as reported in Comparative Example 2. The resulting silver-exchanged, alumina bound and zeolite Y-containing adsorbent contained 13.2 wt % Ag, had a zeolite framework silica/alumina ratio of 10:1 and had an ABD of 0.71 g/cc.

A breakthrough test was performed using the same feed and conditions as specified in Comparative Example 2. The samples size was reduced from 50 cc to 9 cc. The same feed and iodide adsorption conditions were utilized as in Comparative Example 2. The run was continued for 22.2 hours with the iodide concentration of effluent stream being maintained below 5 ppb on a weight basis. At that time iodide breakthrough (i.e. iodide content of effluent rose above 10 ppb) occurred and iodide concentration in the effluent rose rapidly to unacceptable level. Based on the amount of iodide adsorpted before breakthrough a iodide capacity was calculated to be 45.6 mg iodide per cc of adsorbent.

Despite the apparent success of the run, the effluent was cloudy and analysis thereof showed significant contamination with alumina indicating binder leeching. These results indicate the alumina is not a preferred binder for long term commercial service although it may be acceptable for short term runs.

EXAMPLE 2

Example 1 was repeated except that zirconia in a wt. ratio of 1 to 4 with zeolite was substituted for alumina as the binder. Breakthrough occurred as in Example 2 at 44.9 mg of iodide per cc of adsorbent. Analysis of the effluent however showed no significant amounts of zirconia and only trace amounts of silica and aluminum indicating that zirconia was a preferred binder for long term commercial service.

EXAMPLE 3

Example 1 was repeated except that an LZ-210 zeolite having a silica to alumina framework ratio of 6.5 and a silica binder were used in a wt. ratio of 1 to 4 with zeolite. The resulting adsorbent contained about 9 wt. % silver and had an ABD of about 0.6 g/cc.

The breakthrough test results indicated that the adsorbent's capacity for iodides was 36 mg of iodide per cc of adsorbent. During the first 3 hours on stream a white precipitate was observed to form in the effluent which analysis showed to be alumina indicating some increase in silica/alumina framework ratio was occurring in situ. This indicates that a higher ratio sieve would be preferred as it would be more stable.

EXAMPLE 4

Example 1 was repeated except that titantia was substituted for alumina as the binder. The resulting adsorbent contained 7.7 wt. % silver and had an ABD of about 0.6 cc/g and as in Example 1 the zeolite to binder weight ratio in the adsorbent was 4:1.

The breakthrough test results showed capacity for iodide removal to be 21 mg/cc of adsorbent.

EXAMPLE 4A

A second sample of the fresh adsorbent from Example 4 was subjected to further exchange procedure by ion-exchanging an additional quantity of silver therein using the same ion-exchange and finishing procedure that was used in preparation of fresh adsorbent. Analysis of the second activated adsorbent showed it to contain 10.1 wt. % silver.

The breakthrough test was then repeated with the same feed and adsorption conditions and it was found that the twice exchanged adsorbent had a capacity of 23 mg of iodide per cc of adsorbent before breakthrough above 10 ppb in the effluent occurred. Thus performance was improved by a factor of about 10%.

EXAMPLE 4B

A sample of the fresh adsorbent from Example 4A was subjected to further exchange procedure as set forth in Example 4A. Analysis of the activated adsorbent showed it to contain 11 wt. % silver.

The breakthrough test of Example 1 was repeated and found to have a capacity of 26 mg of iodide per cc of adsorbent. This represents a further improvement of 13% over the fresh Example 4A adsorbent performance and is strong evidence of the beneficial efforts of the multiple exchanged procedures of the instant invention.

EXAMPLE 5

Example 4 was repeated except that the binder was zirconia and the method of preparation was by the oil drop procedure described herein before. The wt. ratio of zeolite to binder was the same (i.e 4:1) and the silver exchanged of the fresh adsorbent was 11.4 wt. %. The breakthrough test results for the fresh adsorbent and the results of 5 reactivation cycles of the spent adsorbents using the re-silver exchanged procedure specified in Example 4A are set forth in Table 1.

TABLE 1

RESULTS OF SIX CYCLES OF USE OF SILVER EXCHANGED LZ-210 & ZIRCONIA BINDER

| Cycle No. | Silver Content in wt. % | Breakthrough Test Capacity in mg/cc of adsorbent |
|---|---|---|
| 1 | 11.4 | 19.1 |
| 2 | NA | 21.3 |
| 3 | NA | 25.2 |
| 4 | NA | 27.9 |
| 5 | NA | 21.7 |
| 6 | NA | 21.7 |

As can be seen from Table 1 the spent adsorbent can be reactivated by re-silver exchanged for at least 5 times without significant loss of adsorbent capacity for iodide.

EXAMPLE 6

Example 3 was repeated except that the LZ-210 zeolite used had a silica to alumina framework ratio of 10:1 and the silica binder was formed by the previously described oil dropping procedure.

The breakthrough test results for three samples of the fresh adsorbents are set forth in Table 2.

TABLE 2

RESULTS OF THREE SAMPLES OF FRESH ADSORBENTS OF SILVER-EXCHANGED LZ-210 WITH SILICA BINDER

| Sample No. | Silver Content in wt. % | Breakthrough Test Results in mg/cc of Adsorbent |
| --- | --- | --- |
| 1 | 10.2 | 18.2 |
| 2 | 10.2 | 19.5 |
| 3 | 10.2 | 20.5 |

These results evidence a reproducibility performance of a silica bound system.

EXAMPLE 7

Example 3 is repeated with a LZ-210 zeolite having a silica/alumina ratio of 10 and with a feed solution in the breakthrough test having hexyl iodide substituted for methyl iodide in average concentration corresponding to about 10 wt. ppm of iodide.

The results of the breakthrough test showed a capacity of adsorbent for this heavier organic iodide compound of 15 mg per cc of adsorbent without any degradation of the zeolite or the binder. Breakthrough did not occur until the 37th day on stream.

EXAMPLE 8

The spent adsorbent is recovered from the sixth cycle of use reported in Example 5 and subjected to the regeneration procedure of the present invention. After water-washing to remove any feed material the spent adsorbent is dried at 300° C. for 2 hours.

The dried adsorbent is then subjected to contact with a dry 50/50 vol. mixture of $H_2$ and $N_2$ at a GHSV (gas flow rate per hour divided by bed volume) of 500 $hr^{-1}$, a pressure of 300 kPa and a temperature of 525° C. for a period of about 20 hours until the gaseous effluent is free of hydrogen iodide.

The resulting iodide-stripped adsorbent is then subjected to a mild oxidation treatment to facilitate oxidation of the elemental silver generated in the hydrogen iodide stripping step.

The breakthrough test used in Example 5 is then repeated with this regenerated adsorbent and reasonable results are achieved.

We claim:

1. A method for treating an acidic organic feed liquid contaminated with detrimental amounts of one or more iodide compounds comprising contacting the acidic organic feed stream in an adsorption zone with a solid inorganic adsorbent comprising a combination of a silica-rich zeolitic molecular sieve, which has been cation-exchanged with silver, mercury, copper, lead, thallium, palladium or mixtures thereof, with a substantially insoluble, porous refractory inorganic oxide binder at adsorption conditions effective to adsorb iodide compounds and to maintain liquid-phase thereby producing a substantially iodide compound-free treated acidic organic liquid.

2. The method of claim 1 wherein the zeolitic molecular sieve is a silica-rich zeolite having a silica to alumina framework mole ratio greater than about 5:1.

3. The method of claim 2 wherein the zeolite is selected from the group consisting of steam-stabilized Y zeolite, LZ-210, Y-85 and mixtures thereof.

4. The method of claim 3 wherein the zeolite is LZ-210.

5. The method of claim 4 where the LZ-210 has a framework silica to alumina ratio greater than 8:1.

6. The method of claim 1 wherein the substantially insoluble porous refractory inorganic binder is selected from the group consisting of alumina, silica, titania, zirconia, chromia, boria, vanadia, magnesia and mixtures thereof.

7. The method of claim 1 where the cation-exchanged metal is silver.

8. The method of claim 1 wherein the solid inorganic adsorbent comprises a combination of a hydrophobic ultrastable zeolite LZ-210 cation-exchanged with silver and having a silica to alumina ratio mole greater than 8:1 with a silica, zirconia or titania binder in an amount such that the zeolite is at least about 70 wt % of the adsorbent and wherein the exchanged silver is about 1 to 15 wt % of the adsorbent material, on an elemental basis.

9. The method of claim 1 where the acidic organic feed liquid contains a carboxylic acid having 1 to 7 carbon atoms and an alkyl iodide having 1 to 10 carbon atoms.

10. The method of claim 9 wherein the carboxylic acid is acetic acid and the alkyl iodide is primarily an alkyl iodide having 1 to 7 carbon atoms.

11. The method of claim 1 wherein the acidic organic feed liquid has a pH of about 2.5 to about 5.

12. The method of claim 1 wherein the solid adsorbent is calcined at a temperature greater than 500° C. prior to cation-exchange.

13. The method of claim 1 wherein the adsorption conditions include a temperature of about 40 to 150° C., a pressure sufficient to maintain liquid phase and a LHSV of about 0.1 to 10 $hr^{-1}$.

14. The method of claim 13 wherein the adsorption conditions are selected to result in a treated acidic organic liquid containing less than 10 ppb iodide.

15. The method of claim 1 wherein the adsorption step is continued until break-through of iodide compounds occurs or is about to occur and thereafter the adsorbent is reactivated by withdrawing the adsorbent from contact with the feed liquid, and contacting the adsorbent with a solution of a salt of silver, mercury, copper, lead, thallium or palladium under ion-exchange conditions until an additional increment of such metal is incorporated therein by ion-exchange.

16. The method of claim 1 wherein the treated acidic organic liquid is subjected to a post treatment step to substantially remove any soluble silica or alumina contained therein.

17. The method of claim 1 wherein the spent solid adsorbent recovered therefrom is subjected to a regeneration step by treating with a gas stream containing hydrogen or a mixture thereof with an inert gas at 350 to 600° C. to produce a hydrogen iodide-containing gaseous effluent stream and a iodide-depleted adsorbent.

18. The method of claim 17 wherein the iodide-depleted adsorbent recovered from the regeneration step is treated with a mild oxidizing agent in order to oxidize silver contained therein and wherein the resulting silver cations are cation exchanged with at least a portion of the active sites in the silica-rich zeolite molecular sieve, thereby regenerating the adsorbent for further use in the iodide adsorption step.

19. The method of claim 17 whereby the hydrogen iodide-containing gaseous effluent stream from the regeneration step is recycled to the process that produced the acidic organic feed liquid.

20. The method of claim 1 wherein the treated acidic organic liquid from the adsorption zone is subjected to a post-treatment step by contacting the treated acidic organic stream with another portion of the solid inorganic adsorbent having the silica-rich zeolitic molecular sieve contained therein in the unexchanged form or exchanged with hydrogen, ammonia, alkali metal or alkaline earth metal at conditions effective to recover any cationic metal released during the iodide-adsorption step of claim 1.

* * * * *